United States Patent [19]
Russell

[11] Patent Number: 5,383,234
[45] Date of Patent: Jan. 17, 1995

[54] RADIOGRAPHIC SYSTEM AND A METHOD FOR USING THE SYSTEM FOR RADIOGRAPHIC EXAMINATION OF TISSUE SPECIMENS

[75] Inventor: Donald G. Russell, Kensington, Conn.

[73] Assignee: Beekley Corporation, Bristol, Conn.

[21] Appl. No.: 116,868

[22] Filed: Sep. 3, 1993

[51] Int. Cl.$^6$ .............................................. H05G 1/28
[52] U.S. Cl. ...................................... 378/164; 378/208
[58] Field of Search ................................ 378/164, 208

[56] References Cited

U.S. PATENT DOCUMENTS

| | | | |
|---|---|---|---|
| 4,993,056 | 2/1991 | Lary | 378/164 |
| 5,020,088 | 5/1991 | Tobin | 378/164 |
| 5,105,457 | 4/1992 | Glassman | 378/164 |

OTHER PUBLICATIONS

"Specboard" Literature by Macbrud Corporation, dated at least as early as Sep. 3, 1992.
"Disposable Radiopathological Grid" Literature by Cook Innoray, dated at least as early as Sep. 3, 1992.
"Chenoweth–Frank Radiopathological Grid Grille Radiopathologique Chenoweth-Frank" Literature by D. R. Chenoweth, M.D. and R. L. Frank, R. T. [R]R.D.M.S., dated at least as early as Sep. 3, 1992.
"Specimen Radiography Device" Literature by E. M. Parker Co., Inc., dated at least as early as Jun. 18, 1991.
"Localization Device Aids Breast Biopsy" Article in *Radiology Today*, dated Nov. 1990.
"Breast Specimen Compressor–Container", Literature by TIP Inc., dated at least as early as Sep. 3, 1992.

*Primary Examiner*—Craig E. Church
*Attorney, Agent, or Firm*—McCormick, Paulding & Huber

[57] ABSTRACT

The present invention provides a radiographic system for transporting and radiographically examining a tissue specimen without the risk of exposing health-care workers to potentially hazardous tissue fluids. The system includes a transparent, sealable, liquid impervious container for receiving the tissue specimen and a tray positioned within the container for supporting the specimen. The tray has a first locating grid printed on one side and a second locating grid, which generates a radiographic image when exposed to xrays, supported on the opposite side of the tray in registration with the first grid. Accordingly, when a tissue specimen is positioned on the first grid and then exposed to xrays, a radiographic image of the specimen superimposed on the image of the second locating grid is produced. Since both locating grids are in registration, any tissue abnormality within the specimen can be precisely located with respect to both grids. A method for using the system to generate radiographic images of a tissue specimen is also disclosed.

19 Claims, 3 Drawing Sheets

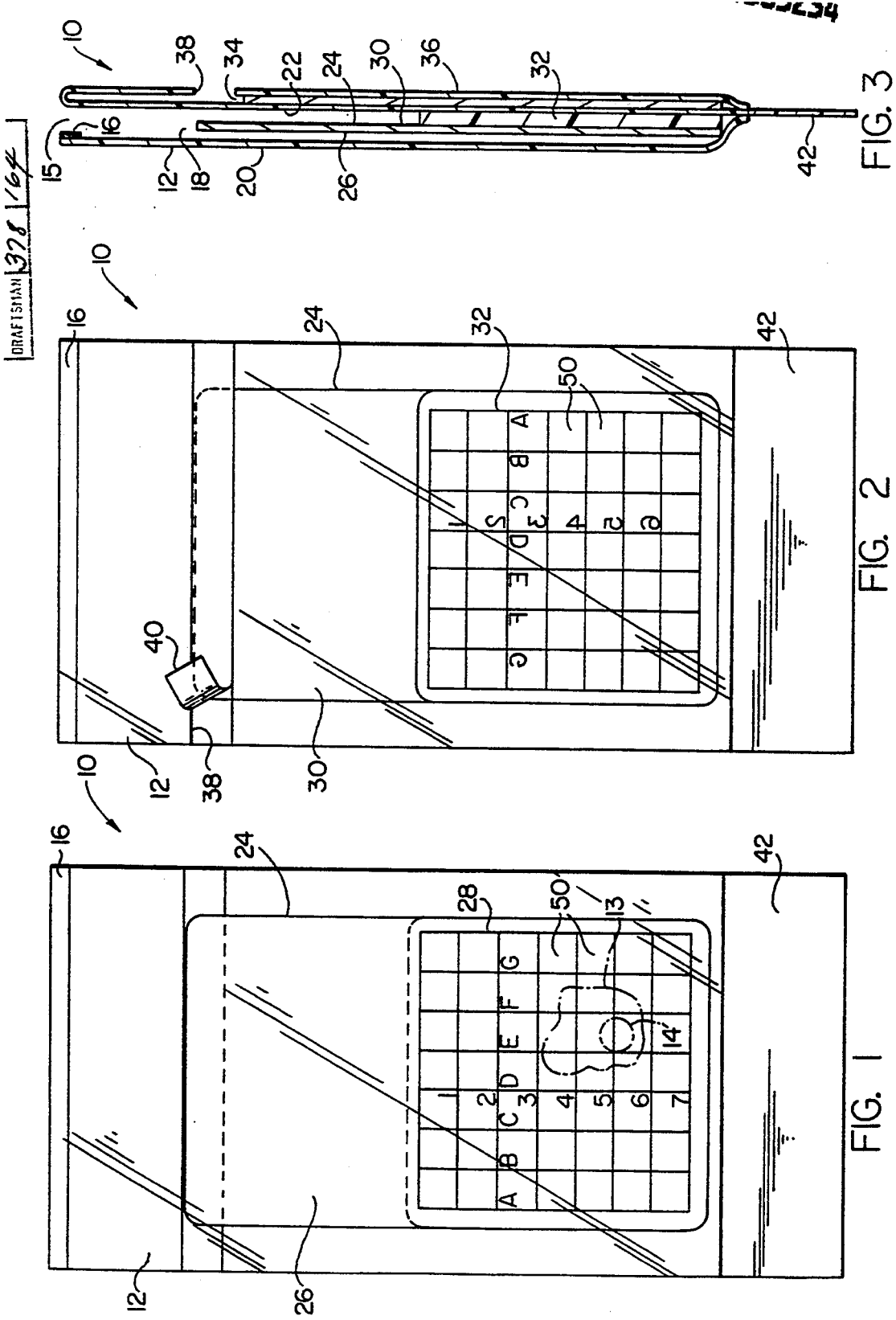

RADIOGRAPHIC SYSTEM AND A METHOD FOR USING THE SYSTEM FOR RADIOGRAPHIC EXAMINATION OF TISSUE SPECIMENS

BACKGROUND OF THE INVENTION

The present invention relates generally to diagnostic radiology and, more particularly, to a system for producing radiographs of surgically biopsied tissue specimens.

Diagnostic radiology procedures often show a tissue abnormality which can only be identified as either malignant or benign by surgical biopsy and subsequent microscopic study. This is most often the case with mammography, the examination of the breast with radiography, where a suspected soft tissue tumor or an abnormal calcification seen on a mammogram frequently is not palpable due to its small size.

Accordingly, the tissue area containing the possible cancer must be localized preoperatively using a well-known needle/guidewire placement technique. The surgeon, guided by an implanted guidewire, removes a block of tissue thought to contain the abnormality. The tissue block is then examined by specimen radiography to determine if it does in fact contain the suspicious tissue. If the radiologist does identify the same abnormal tissue features seen during the initial radiological examination, the surgical portion of the procedure is concluded.

The abnormal tissue, which is frequently less than a centimeter in diameter, must then be localized within the larger tissue block, which usually ranges between 6 to 10 cm in diameter. Typically, the pathologist responsible for performing the microscopic examination of the abnormality cannot accurately identify it either by feel or by grogs tissue sectioning. Thus, the radiologist must assist the pathologist by precisely describing the area within the tissue block where the abnormality is located. Once the abnormality has been accurately localized, the pathologist excises a segment measuring 10 to 15 mm in diameter for fixation, sectioning, staining and microscopic examination.

In the past, it has been common practice to examine the tissue block while the block is placed on a radiographically visible grid. This practice presents a number of drawbacks, however. First, the superimposed shadow cast by the grid may obscure fine radiographic detail in the tissue block. This could cause the radiologist to mis-identify or fail completely to identify the location of the abnormality within the block.

Second, radiologists, lab technicians and other health-care workers find it difficult to handle and radiograph tissue specimens and, at the same time, prevent personal exposure to tissue fluids and equipment contamination. This is of particular concern in view of a recent program instituted by the Occupational Safety and Health Administration (OSHA) to enforce safety standards intended to limit occupational exposure to body tissues, blood and other tissue fluids.

Pursuant to these standards, every employer is required to anticipate and identify any such exposure in the workplace and provide protective equipment, an exposure control plan, appropriate safety devices and an employee educational program. Further, all body fluids and tissues from all patients must be treated as potentially lethal. At a minimum these so-called "universal precautions" will require gloves, gowns, masks, face shields and safe needle and tissue fluid disposal when conducting tissue specimen radiography.

It is, therefore, an object of the invention to provide a system for specimen radiography wherein the location of an abnormality within a tissue block can be easily and precisely identified.

It is a further object of the invention to provide such a system wherein fine radiographic detail within the tissue block is left completely unobscured.

It is a still further object of the invention to provide a system wherein a tissue specimen can be transported, manipulated and examined radiographically and by ultrasound without the risk of exposing health-care workers to potentially hazardous tissue fluids or contaminating equipment with such fluids.

SUMMARY OF THE INVENTION

The present invention meets these and other objects by providing a radiographic system which permits tissues specimens to be transported and radiographically examined without the risk of exposing health-care workers to tissue fluids. The system includes a transparent, sealable, liquid impervious container for receiving a tissue specimen. Positioned inside the container is a tray which has a first locating grid supported on a first side of the tray and a second locating grid supported on the opposite side of the tray. The second locating grid includes grid lines that generate a radiographic image when exposed to xray radiation. The locating grids are in registration with one another; thus, when the tissue specimen is placed on the first grid and exposed to xrays, any abnormality within the specimen appears at precisely the same location on both grids. Accordingly, the location of the abnormality within the specimen can be accurately determined.

The tray is formed form a substantially fluid impervious material which prevents tissue fluids from completely penetrating through from the first side of the tray to its opposite side. Accordingly, any tissue fluid contacting the first side of the tray cannot completely penetrate the tray and interfere with the second locating grid. In the preferred embodiment of the invention, the tray is formed from fluid impervious cardboard, The system further includes means for securing the tissue specimen to the first side of the tray in a fixed position. In the preferred embodiment, the tissue is secured to the tray by means of an absorbent material paper combined with the cardboard from which the tray is formed. Only enough paper is added to permit tissue fluid absorption at the surface of the tray when the tissue specimen is placed thereon. It has been found that this limited absorption is sufficient to maintain the specimen in a fixed position with respect to the tray.

While this is the preferred means for maintaining the specimen in a fixed position on the tray, other suitable means may also be employed. For example, the tray could be coated with a radiolucent adhesive that would bond the specimen to the tray. Clamping means could also be employed as long as they did not interfere with the radiographic image of the specimen and the second locating grid.

Preferably, the container is formed from a flexible material which permits manipulation of the tissue specimen from outside the container. Thus, radiologists and other health-care workers can position the tissue specimen on the tray without exposure to tissue fluids. The container is also preferably formed from a material which permits the uninterrupted transmission of sound waves so that ultrasound images of the specimen can also be generated.

In another aspect, the invention also relates to a method for transporting and radiographically examining a tissue specimen without the risk of exposing health-care workers to tissue fluids. A radiographic system is provided which includes the container, tray and locating grids discussed above. The tissue sample is positioned on the tray in a fixed position and then sealed within the container. Finally, the tissue sample is exposed to xray radiation while the specimen is fixed to the tray and sealed in the container to generate an xray image of the specimen superimposed on the second locating grid.

BRIEF DESCRIPTION OF THE DRAWINGS

FIG. 1 is a front view of a radiographic system according to the invention with a tissue specimen positioned on the tray.

FIG. 2 is a back view of the radiographic system shown in FIG. 1.

FIG. 3 is a cross-sectional view of the radiographic system shown in FIG. 1.

DETAILED DESCRIPTION OF THE INVENTION

Figure 4:
FIG. 4 is a photograph of a specimen radiograph made according to the invention.

FIGS. 1-3 illustrate a system for radiographically examining a tissue specimen. The system 10 comprises a flexible, transparent, sealable, liquid impervious bag 12 for receiving a tissue specimen 13 having an abnormality 14 contained therein. The bag has an opening 15 provided with a resealable adhesive strip 16. Of course, the opening 15 could be sealed by other suitable fluid-tight closures. The opening 15 provides access to a pocket 18 defined by walls 20 and 22 for receiving the specimen. In general, the pocket 18 is large enough to accommodate multiple tissue specimens from the same patient, each specimen measuring up to 12 or more centimeters in diameter.

The pocket 18 contains a tray 24 for supporting the tissue specimen 13. The tray has a first side 26 with an alphanumeric locating grid 28 printed thereon. The opposite side 30 of the tray 24 supports a second alphanumeric locating grid 32 in registration with the first locating grid 28 on the first side of the tray. The grid 32 is formed from a low density material, and the grid lines and alphanumeric designations comprising grid 32 generate a radiographic image when exposed to xrays. Preferably, grid 32 is made from plastic, and the grid lines and alphanumeric designations are grooves formed in the plastic. Air within the grooves provides them with a greater radiolucency relative to that of the plastic. To maintain the correct radiolucency of the grooves, they must be kept free of fluid. This is accomplished by directly attaching grid 32 to side 30 of the tray to seal the grooves against the entry of fluid. Like the bag 12, the tray 24 is large enough to accommodate multiple tissues specimens from the same patient.

After the surgeon removes the tissue specimen from the patient, it is placed on grid 28 on side 26 of the tray, and the pocket 18 is sealed. The specimen is then transported to radiology for examination. As those skilled in the art well-know, compression of the specimen is a very important aspect of specimen radiography. This tends to displace air from the tissue and produces a more uniform tissue thickness and uniform fine image density. In actual practice, the bag 12 containing the tissue specimen is placed on a standard mammography xray table or tray and an associated paddle is lowered to compress the tissue. The degree of compression can be controlled by the operator, and mild to moderate compression is necessary to obtain the desired uniform thickness.

Those skilled in the art also recognize that some tissue abnormalities, particularly breast abnormalities, can only or primarily be visualized by ultrasound. Since such abnormalities may also not be palpable, they must be localized by ultrasound prior to surgery. Further, after surgical biopsy, the only way to be sure that such an abnormality is present in the removed tissue specimen is to examine the specimen with ultrasound.

To meet these objectives the bag 12 is made from a flexible material which permits mild to moderate compression of the specimen while it is sealed within the bag. Moreover, the material forming the bag provides for the uninterrupted transmission of sound waves so that the specimen may be subjected to adjunctive ultrasound imaging. In the illustrated embodiment, the bag 12 is made from plastic, although any other flexible material meeting these criteria would, of course, be acceptable. The bag's flexibility also permits the radiologist or other health care workers to further position the specimen with respect to grid 28 without direct contact with the specimen. Thus, the specimen is transported and manipulated for radiographic examination without the risk of exposing health-care workers to possibly hazardous tissue fluids and without the risk of equipment contamination.

Referring again to the tray 24 in more detail, the tray is formed from a substantially fluid impervious cardboard which is free from radiopaque artifacts and patterns. The cardboard includes a quantity of absorptive material sufficient to permit limited absorption of tissue fluid at the surface of the tray. The tray is constructed in this manner because tissue fluid absorbed on side 26 has proven effective in maintaining the specimen in a fixed position with respect to the tray while the specimen is being transported, examined and sectioned. In the illustrated embodiment the absorptive material is an absorptive paper combined with the cardboard. It has been found that Carolina Coated Blank paper available from Federal Paper Co. is particularly useful in this regard.

However, it is important that fluid absorption be limited to the surface of the tray only, since any fluid penetrating entirely through to opposite side 30 might enter the grooves forming alphanumeric grid 32. If this occurs, fluid entering the grooves might interfere with the radiographic shadow cast by the grid. Since the grooves formed in grid 32 are immediately adjacent side 30 of the tray, the tray seals the grooves and prevents fluid from entering therein.

In the preferred embodiment of the system, bag 12 further comprises an integral pocket 34 defined by walls 22 and 36 for storing requisition slips or other forms of documentation. Wall 36 is provided with an opening 38 which allows access to pocket 34. Opening 38 is formed by pull tab 40. As is evident from the drawings, wall 22 and adhesive closure 16 isolate pocket 34 and any documentation contained therein from pocket 18. The bag 12 is also provided with an integral patient identification label 42. Since the label 42 is integral with the bag, the chances of associating a particular tissue specimen with the wrong patient are greatly reduced. Further, the label may also include the grid coordinates of the identified tissue abnormality, allowing direct communication of the coordinates to the pathologist without error, as will be explained in more detail below.

Turning now to the method of using the system 10 for specimen radiography, it will be appreciated that since locating grid 32 generates a radiographic image when exposed to xrays, an xray image of specimen 13, when positioned on locating grid 28, will show the specimen superimposed on grid 32. By referring to the radiographic image of the specimen superimposed on the grid 32, the pathologist can pinpoint the location of the abnormality within the specimen to within a few millimeters using grid 28.

Figure 5:
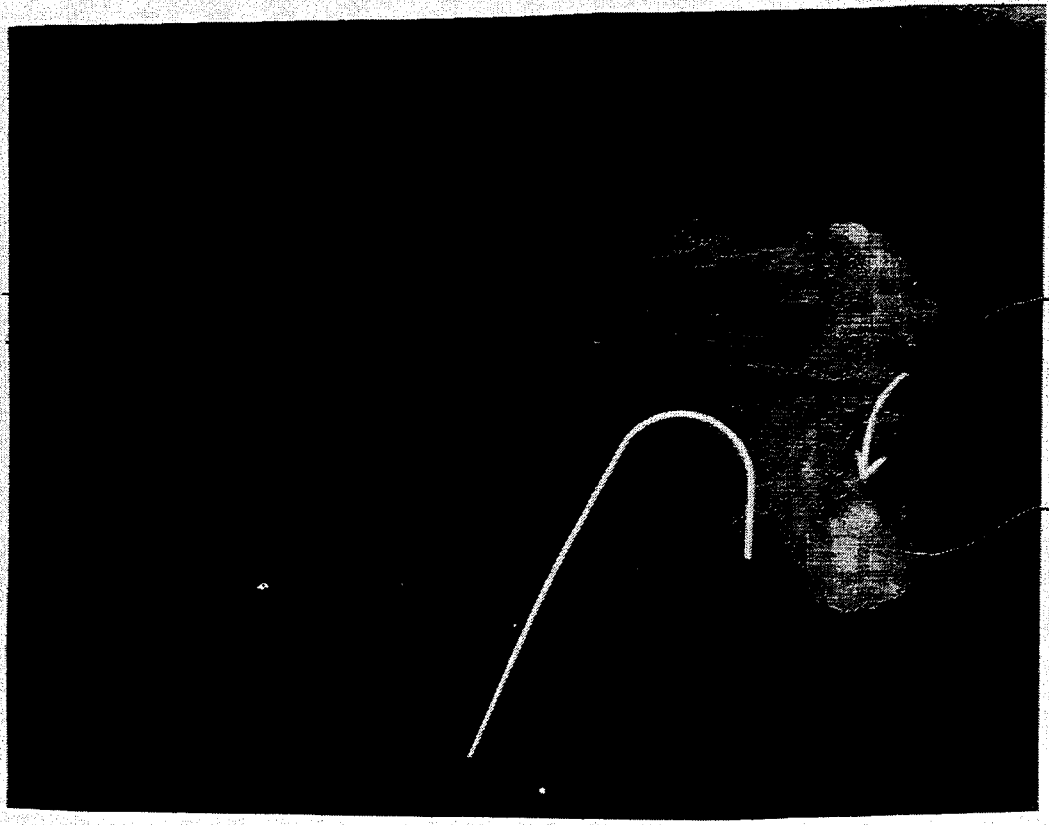
FIG. 5 is a photograph of a second specimen radiograph made according to the invention.

Thus, any abnormality, such as abnormality 14, contained within the specimen can be identified and precisely located with respect to both grids. This is illustrated by FIGS. 4 and 5 which are photographs of tissue specimen radiographs made using the invention. FIGS. 4 shows a tissue specimen 41 containing abnormal calcifications 43 and a small rounded abnormality 44 which prompted the biopsy. FIG. 5 shows a specimen 46 containing an oval-shaped abnormality 48 superimposed on the grid at sector G5. Since the bag is flexible, the specimen can be palpated through the bag which may allow the pathologist to either locate the abnormality by manipulation or locate an area within the specimen which may have been stained by a localizing dye, such as methylene blue, as part of the surgical biopsy procedure.

Figure 6:
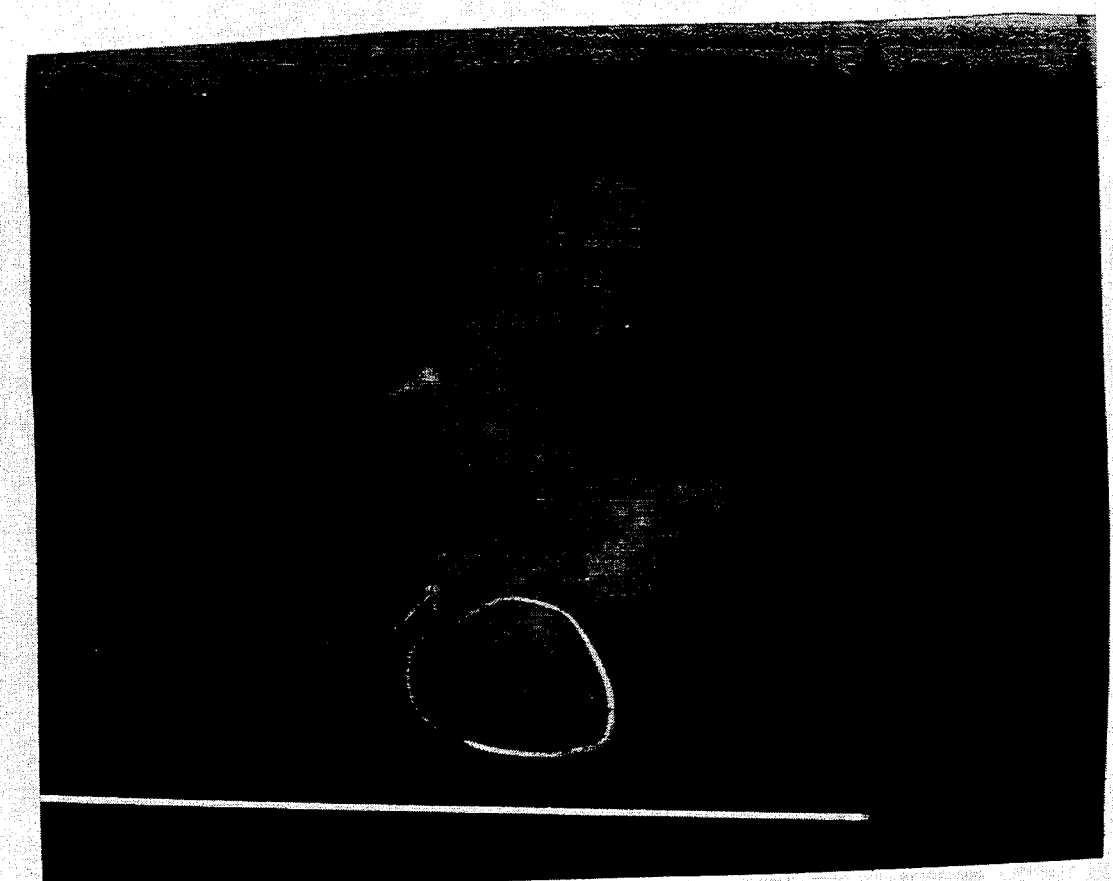
FIG. 6 is a magnification projection of FIG. 4.
Figure 7:
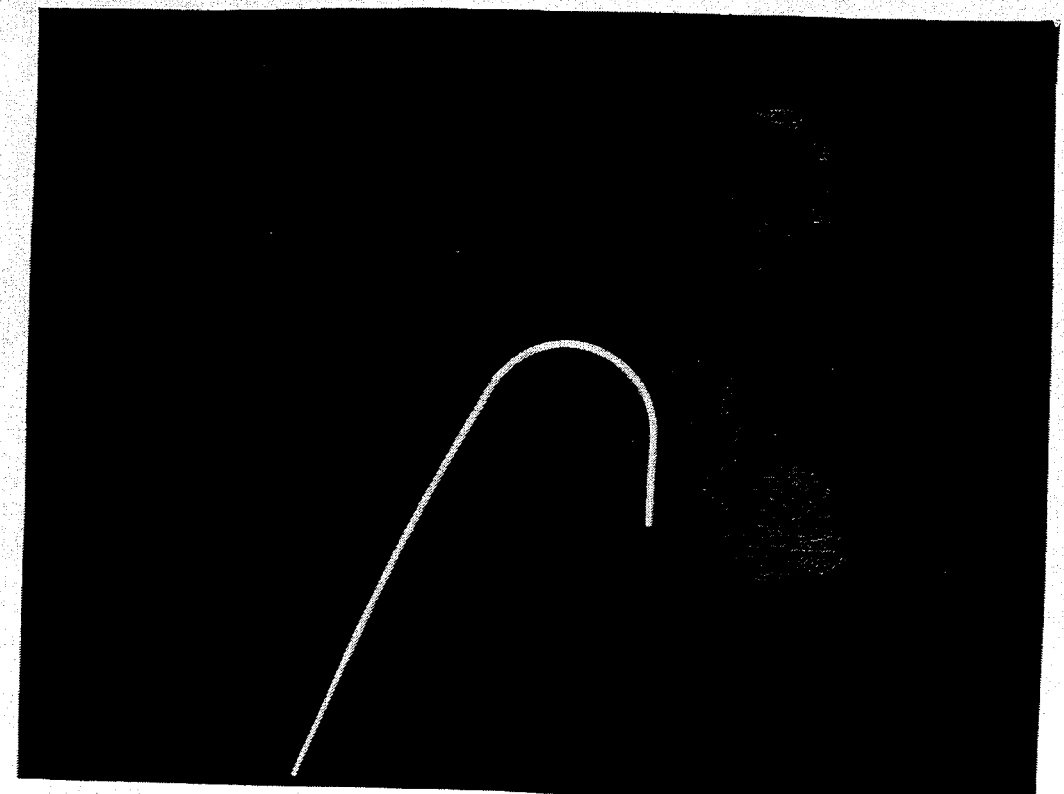
FIG. 7 is a magnification projection of FIG. 5.

Current mammography frequently includes radiographical magnification views of a breast for improved soft tissue detail and detailed examination of possible malignant calcitic deposits. The present invention permits similar corresponding specimen magnification views which may be compared to the original mammograms to ensure that the abnormal tissue is included within the excised specimen. This aspect of the invention is illustrated in FIGS. 6 and 7 which are, respectively, magnification projections of FIGS. 4 and 5. Since the alphanumeric designations are located within the area of grid 32 defined by the grid lines., and not on the perimeter of the grid, the designations remain in the field of view even when the radiographic image is magnified.

As will be appreciated by those skilled in the art, the density of the material from which grid 32 is formed and the construction of the grooves must be such that the grid generates a clear radiographic image which projects through the image of the specimen but, at the same time, does not obscure fine tissue detail. As noted above the grid 32 is made of plastic, and the air within the grooves provides them with a greater radiolucency relative to that of the plastic. This is why it is imperative that fluid be kept from entering the grooves. It is also important that the size of the sectors 50, 50 defined by the grid lines be dimensioned to provide accurate localization of the abnormality with out introducing confusing radiographic shadows. Generally, the sectors measure from about 10 to about 20 mm on a side. Finally, since the opening 15 is fluid-impervious and resealable, the tray 24 can be placed within the bag, sealed and the entire system sterilized so that it can be introduced without concern of contamination into the surgical field during the biopsy.

While preferred embodiments have been shown and described, various modifications and substitutions may be made without departing from the spirit and scope of the invention. Accordingly, it is to be understood that the present invention has been described by way of example and not by limitation.

I claim:

1. A radiographic system for transporting and radiographically examining a tissue specimen without risk of exposure to tissue fluid, said system comprising:
   a transparent, sealable, liquid impervious container for receiving a tissue specimen;
   a tray having a first side and an opposite side positioned within the container for supporting a tissue specimen on said first side, said tray comprising a substantially fluid impervious material;
   a first locating grid supported on the first side of the tray;
   a second locating grid supported on the opposite side of the tray in registration with the first locating grid, the second locating grid including grid lines which generate a radiographic image when exposed to xray radiation, and
   means for securing the tissue specimen to the first side of the tray in a fixed position.

2. The system of claim 1 wherein the second locating grid comprises a low density material, and the grid lines which generate the radiographic image are grooves formed in the material.

3. The system of claim 2 wherein the low density material further includes alpha-numeric grooves formed therein.

4. The system of claim 1 wherein the container is flexible to permit manipulation of the tissue specimen from outside the container when the specimen is sealed within the container.

5. The system of claim 3 wherein the low density material is plastic.

6. The system of claim 4 wherein the first locating grid is sealed to prevent fluid form entering the grooves.

7. The system of claim 1 wherein the tray is free of radiopaque artifacts and patterns.

8. The system of claim 1 wherein the transparent container permits the uninterrupted transmission of sound waves therethrough.

9. A radiographic system for transporting and radiographically examining a tissue specimen without risk of exposure to tissue fluid, said system comprising:
   a flexible, transparent, sealable, liquid impervious container for receiving a tissue specimen;
   a tray having a first side and an opposite side positioned within the container for supporting a tissue specimen on said first side, said tray comprising a substantially fluid impervious cardboard free from radiopaque artifacts and patterns, the cardboard including a quantity of absorptive material which permits surface absorption of fluid from the tissue specimen by the tray to maintain the specimen in a fixed position on the tray;
   a first locating grid supported on the first side of the tray;
   a second locating grid supported on the opposite side of the tray, the second locating grid including grid lines which generate a radiographic image when exposed to xray radiation.

10. The system of claim 9 wherein the second locating grid comprises a low density material, and the grid lines which generate the radiographic image are grooves formed in the material.

11. The system of claim 10 wherein the low density material further includes alpha-numeric grooves formed therein.

12. The system of claim 11 wherein the second locating grid is an alpha-numeric grid printed on the first side of the tray.

13. The system of claim 9 wherein the first locating grid is sealed to prevent fluid form entering the grooves.

14. The system of claim 9 wherein the transparent container permits the uninterrupted transmission of sound waves therethrough.

15. The system of claim 9 wherein the container further comprises an integral pocket for receiving documentation.

16. The system of claim 9 wherein the container further comprises a patient information label.

17. A method for transporting and radiographically examining a tissue specimen without risk of exposure to tissue fluid, said method comprising the steps of:

providing a radiographic system including a transparent, sealable, liquid impervious container for receiving a tissue specimen, a tray having a first side and an opposite side positioned within the container for supporting a tissue specimen on said first side, a first locating grid supported on the first side of the tray, and a second locating grid supported on the opposite side of the tray in registration with the first locating grid, the second locating grid including grid lines which generate a radiographic image when exposed to xray radiation;

positioning the tissues sample on the locating grid in a fixed position;

sealing the tissue sample fixed to the tray in the container, and exposing the tissue sample to xray radiation while the specimen is fixed to the tray and sealed in the container to generate an xray image of the specimen superimposed on the second locating grid.

18. The method of claim 17 wherein the container is flexible and the step of positioning is further characterized in that the tissue sample is manipulated with respect to the tray from the outside of the container.

19. The method of claim 17 further including the step of subjecting the tissue sample to ultrasound examination while the specimen is fixed to the tray and sealed in the container.

* * * * *